United States Patent
Tanabe et al.

[11] Patent Number: 5,853,728
[45] Date of Patent: Dec. 29, 1998

[54] POLYPHENOLIC COSMETIC COMPOSITION

[75] Inventors: Masayuki Tanabe, Matsudo; Tomomasa Kanda, Kashiwa; Akio Yanagida, Tokyo; Toshihiko Shoji, Nagareyama, all of Japan

[73] Assignee: The Nikka Whisky Distilling Co., Ltd., Tokyo, Japan

[21] Appl. No.: 773,596

[22] Filed: Dec. 27, 1996

[30] Foreign Application Priority Data

Dec. 28, 1995 [JP] Japan .................................. 7-342603

[51] Int. Cl.[6] .................................................. A01N 65/00
[52] U.S. Cl. .......................... 424/195.1; 424/59; 424/60; 424/63; 514/2; 514/8; 514/54; 514/783; 514/846; 514/847
[58] Field of Search .................................. 424/195.1, 59, 424/60, 63; 514/783, 2, 8, 826, 54, 59, 846, 847

[56] References Cited

U.S. PATENT DOCUMENTS

| | | | |
|---|---|---|---|
| 3,436,407 | 4/1969 | Masquelier | 260/345.2 |
| 4,508,714 | 4/1985 | Cecic et al. | 424/195.1 |
| 4,511,559 | 4/1985 | Szendrei et al. | 514/54 |
| 4,698,360 | 10/1987 | Masquelier | 514/456 |
| 4,774,226 | 9/1988 | Lewenstein | 514/8 |
| 5,518,722 | 5/1996 | Szaloki et al. | 424/195.1 |

OTHER PUBLICATIONS

L/AMI (Publisher: Arban Muller/ Sep. 1995 Sun Care Issue No. 12).

Terao et al., "Protective Effect of Epicatechin, Epicatechin Gallate, and Quercetin on Lipid Peroxidation in Phospholid Bilayers", Archives of Biochemistry and Biophysics, vol. 308, No. 1, pp. 278–284 (Jan. 1994).

Sakanaka et al., "Inhibitory Effects of Green Tea Polyphenols on Glucan Synthesis and Cellular Adherence of Cariogenic Streptococci", Agric. Biol. Chem., 54(II), pp. 2925–2929 1990.

Vigorov, L. L., "Catechins in Apples", Fenol'nye Soedin. Ikh Biol. Funkds,. Mater. Vses. Simp., 1st (1968), vol. 202–8, (abstract and English translation). (1968).

Kakegawa et al., "Inhibitory effects of some natural products on the activation of Hyaluronidase and Their Anti–allergic Actions", Chem. Pharm. Bull. 49(6), pp. 1439–1442 (Jun. 1992).

*Primary Examiner*—Terressa Mosley
*Attorney, Agent, or Firm*—Armstrong, Westerman Hattori, McLeland & Naughton

[57] ABSTRACT

Cosmetics are herein disclosed which contain a polyphenol derived from the fruits of Rosaceae, and the polyphenol is obtainable by purifying a pressed juice or an extract of the unripe fruits of the Rosaceae, for example, apples, pears or peaches. The cosmetics have many useful functions such as an ultraviolet light absorbing activity and a free radical erasing activity.

9 Claims, 1 Drawing Sheet

POLYPHENOLIC COSMETIC COMPOSITION

BACKGROUND OF THE INVENTION (i) Field of the Invention

The present invention relates to cosmetics such as a skin cosmetic material and a hair cosmetic material.

(ii) Description of Related Art

The wide concept of cosmetics includes a skin cosmetic material, a hair cosmetic material and a toothpaste. Functions which the cosmetics should possess depend upon each of their kinds. For example, a milky lotion and a cream aim at beautiful skin, and so in these cosmetics, the function of well-regulating the skin is required. Moreover, a soap aim at washing, and so in the soap, a washing function is required. In recent years, however, further additional functions have been required in addition to these functions which the cosmetics should possess. Examples of these additional functions include an antiallergic activity, an ultraviolet light absorbing activity and a free radical erasing activity for the skin cosmetic material, and an anticariogenic activity and a deodorant activity for the toothpaste.

Particularly, at present, from the viewpoint of protecting the skin from ultraviolet light increased due to the reduction of an ozone layer to prevent sunburn and hence the outbreak of skin cancer, the function of absorbing the ultraviolet light in an extensive wavelength range is regarded as important. In addition, from the viewpoint of preventing the skin cancer and the aging of the skin, a free radical erasing activity is also regarded as important. Moreover, as a recent tendency, it has been required that a single cosmetic has many additional functions.

SUMMARY OF THE INVENTION

In view of such circumstances, the present invention has been developed, and an object of the present invention is to provide cosmetics having an ultraviolet light absorbing activity in an extensive wavelength range, a free radical erasing activity, an antiallergic activity and other functions.

The present inventors have intensively investigated with the intention of solving the above-mentioned problems, and as a result, it has been found that a polyphenol contained in large quantities in the fruits of Rosaceae, particularly the unripe fruits of apples, pears, peaches and the like has many physiological activities inclusive of the ultraviolet light absorbing activity and the free radical erasing activity. In consequence, the present invention has been completed.

That is to say, according to the present invention, there can be provided cosmetics containing a polyphenol derived from the fruits of the Rosaceae. In the cosmetics of the present invention, the polyphenol derived from the fruits of the Rosaceae is preferably obtained by purifying a pressed juice or an extract of the unripe fruits of the Rosaceae. The polyphenol derived from the fruits of the Rosaceae contained in the cosmetics of the present invention is preferably derived from apples, pears or peaches. In the present invention, the polyphenol derived from the fruits of the Rosaceae has a maximum ultraviolet light absorption wavelength in the range of 280 to 290 nm and in the range of 315 to 325 nm. Furthermore, in the present invention, the polyphenol derived from the fruits of the Rosaceae has a free radical erasing activity of $1.0 \times 10^1$ to $1.0 \times 10^6$ units/g as measured by an electron spin resonance method (an ESR method).

DETAILED DESCRIPTION OF THE INVENTION

Figure 1:
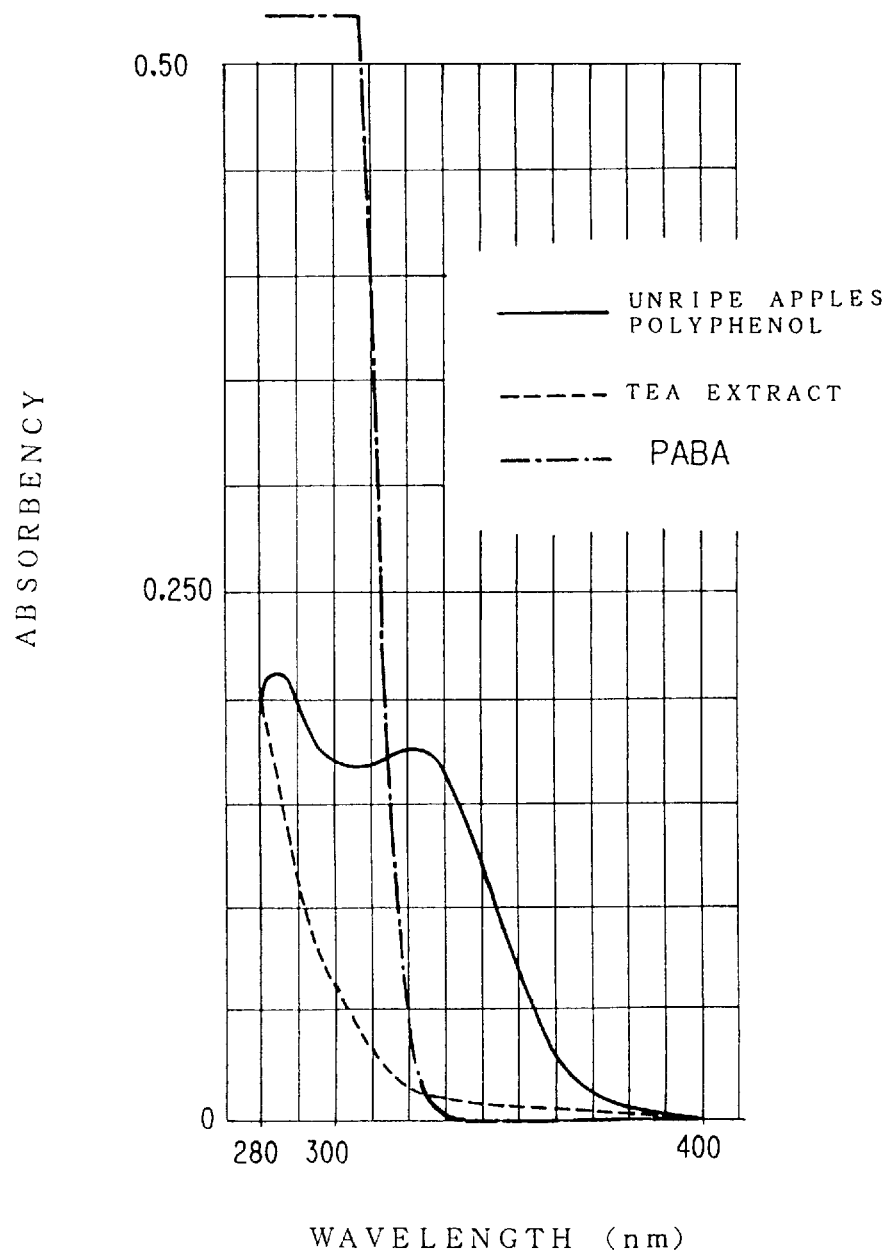
FIG. 1 is a graph showing an ultraviolet light absorbing activity of a polyphenol derived from the fruits of Rosaceae.

Cosmetics of the present invention contain a polyphenol derived from the fruits of Rosaceae. It has been elucidated that the polyphenol contains simple polyphenol compounds such as caffeic acid derivatives, p-coumaric acid derivatives, flavan-3-ols (catechins), flavonols (quercetin glycosides) and dihydrochalcones (phloretin glycosides), and high-molecular polyphenol compounds such as condensed tannins (Japanese Patent Application Laid-open No. 285876/1995). Therefore, the above-mentioned fruits polyphenol has various physiological functions.

As the first physiological function which the polyphenol derived from the fruits of the Rosaceae has, there is an ultraviolet light absorbing activity. Therefore, when the above-mentioned polyphenol is mixed with the cosmetics, the ultraviolet light absorbing activity can be imparted to the cosmetics.

The ultraviolet light absorbing activity, which the above-mentioned polyphenol has, is shown in FIG. 1.

The ultraviolet light can be classified into a short wavelength ultraviolet light having a wavelength of 280 nm or less (hereinafter referred to as "UV-C"), a medium wavelength ultraviolet light having a wavelength of 280 to 320 nm (hereinafter referred to as "UV-B") and a long wavelength ultraviolet light having a wavelength of 320 to 400 nm (hereinafter referred to as "UV-A"). Of these ultraviolet lights, most of the UV-C is absorbed by an ozone layer, and therefore the ultraviolet lights which have an influence on the skin are mainly the UV-A and the UV-B.

As substances having the ultraviolet light absorbing activity, there are heretofore known various compounds such as paraaminobenzoic acid (hereinafter referred to as "PABA"), dibenzoylmethane and cinnamates. However, the above-mentioned polyphenol is different from these substances, and it is a natural component derived from vegetables and has a maximum ultraviolet light absorption wavelength in the range of 280 to 290 nm and in the range of 315 to 325 nm as shown in FIG. 1. Therefore, the absorption frequency belt of the polyphenol ranges from the UV-B to the UV-A, which is wider as compared with that of these substances. Therefore, the cosmetics of the present invention can exert the ultraviolet light absorbing activity to prevent sunburn and the outbreak of skin cancer.

As the second physiological function which the above-mentioned polyphenol has, there is a free radical erasing activity. Therefore, when the above-mentioned polyphenol is mixed with the cosmetics, the free radical erasing activity can be imparted to the cosmetics.

It is known that the free radical causes the skin cancer, the aging of the skin and the like, and is concerned with sunlight dermatitis, atopic dermatitis and the like.

The above-mentioned polyphenol shows a free radical erasing activity of $1.0 \times 10^1$ to $1.0 \times 10^6$ units/g as measured by an electron spin resonance method (an ESR method), and the polyphenol derived from unripe apples or the like shows a free radical erasing activity as high as $1.7 \times 10^5$ units/g. The free radical erasing activities of the various vegetable extracts have been reported by Kuramoto ["Foods and Development", Vol. 27, No. 3, p. 22–23, (1992)], but the polyphenol derived from the fruits of the Rosaceae belongs to a group having the highest free radical erasing activity among these reported vegetable extracts. Therefore, the cosmetics of the present invention can exert the above-mentioned free radical erasing activity to suppress the outbreak of the skin cancer and the aging of the skin and to prevent the atopic dermatitis and the like.

It has been confirmed that the condensed tannins contained in the above-mentioned polyphenol contains a component having the function of disturbing the work of an angiotension I converting enzyme (hereinafter referred to as "ACA") which is an enzyme regarding the rise of blood pressure (Japanese Patent Application Laid-open No. 285876/1995). Therefore, the above-mentioned polyphenol has a blood pressure lowering activity as the third physiological activity, and when the polyphenol is mixed with cosmetics, particularly bath cosmetics such as a bath agent, the blood pressure lowering activity can be imparted to the cosmetics.

Furthermore, the above-mentioned polyphenol has an antimutagenic activity as the fourth physiological activity (Japanese Patent Application Laid-open No. 285876/1995). The results of many recent researches have reported that a high interrelation is present between carcinogenesis and a mutagenic activity, and therefore when the above-mentioned polyphenol is mixed with the cosmetics, the exertion of a carcinogenesis preventing function can be expected.

In addition, the above-mentioned polyphenol has a Hyaluronidase-inhibiting activity and a histamine release suppressing activity (Japanese Patent Application Laid-open No. 285876/1995). Therefore, the polyphenol has an antiallergic activity as the fifth physiological activity, and when the above-mentioned polyphenol is mixed with the cosmetics, particularly a skin cosmetic material such as a milky lotion or a foundation cream, the antiallergic activity can be imparted to the cosmetics, so that the outbreak of the atopic dermatitis can be prevented.

It has also been confirmed that the above-mentioned polyphenol hinders the activity of glucosyltransferase, produced by oral Streptococcus, regarding the formation of deposit which is an important factor of dental caries (decayed tooth) (Japanese Patent Application Laid-open No. 285876/1995). Therefore, the polyphenol has an anticariogenic activity as the sixth physiological activity, and when the above-mentioned polyphenol is mixed with the cosmetics, particularly a toothpaste, the anticariogenic activity can be imparted to the toothpaste.

It has also been confirmed that the above-mentioned polyphenol shows a deodorant activity and a production suppressing activity to volatile sulfur compounds such as hydrogen sulfide, methyl mercaptan and dimethyl sulfide which are odorous components derived from foods and which cause halitosis (Japanese Patent Application Laid-open No. 285876/1995). Therefore, the polyphenol has the deodorant activity as the seventh physiological activity, and when the above-mentioned polyphenol is mixed with the cosmetics, particularly the toothpaste, the deodorant activity can be imparted to the toothpaste, so that the generation of the halitosis can be prevented.

It has also been confirmed that the above-mentioned polyphenol shows a tyrosinase hindering activity to inhibit the production of melanin ["Japanese Food Science Engineering Association", 42nd, Lecture Booklet, p. 180 (1995), and "Tissue Culture", Vol. 21 (8), p. 293–297 (1995)]. Therefore, the polyphenol has the melanin production inhibiting activity as the eighth physiological activity, and when the above-mentioned polyphenol is mixed with the cosmetics, particularly a skin cosmetic material such as the milky lotion or the foundation cream, the melanin production inhibiting activity can be imparted to the skin cosmetic material, so that a pigmentation disease of stains or the like can be prevented.

The above-mentioned polyphenol has a dandruff inhibiting activity and a sterilizing activity in addition to the above-mentioned physiological activity, and so when the polyphenol is mixed with a hair cosmetic material such as a shampoo, the dandruff inhibiting activity can be imparted to the hair cosmetic material. Alternatively, when the polyphenol is mixed with selected cosmetics, the sterilizing activity can be imparted to the cosmetics.

In the present invention, examples of the cosmetics include skin cosmetic materials such as soaps, facial cleaning materials, creams, milky lotions, face toilet lotions, colognes, shaving creams, shaving lotions, toilet oils, sunburn and sunscreen lotions, sunburn and sunscreen oils, face powders, foundation creams, perfumes, facial packs, nail creams, enamels, enamel removing liquids, eyebrow pencils, rouges, ice creams, eye shadows, mascaras, eye liners, lipsticks, lip creams and bath cosmetics, hair cosmetic materials such as shampoos, rinses, hair dyes and head hair cosmetic materials, toothpastes, medicinal cosmetics, medicinal toothpastes and quasi-drugs such as bath agents.

The soaps include soaps which can be thrown into a bathtub. Furthermore, the shaving creams and the shaving lotions include creams and lotions which can be used at and after the shaving. The bath cosmetics mean bath cosmetics which can be thrown into the bathtub for the purposes of cleaning a body and enjoying a smell and for another similar purpose.

As described above, the cosmetics of the present invention contain the polyphenol derived from the fruits of the Rosaceae, but the purification of this polyphenol can be carried out by treating the pressed juice or the extract of the fruits with an adsorbent. That is to say, the polyphenol is contained in a fraction adsorbed by the adsorbent (hereinafter referred to as "the adsorbed fraction"), and this adsorbed fraction is eluted with a water-containing alcohol (ethanol or the like) to obtain the polyphenol.

Examples of the fruits of the Rosaceae include apples, pears and peaches, but above all, the apples are particularly preferable. The ripe fruits and the unripe fruits can both be used, but the unripe fruits are more preferable, because they contain a larger amount of the polyphenol and also contain various components having many physiological activities in large quantities. Furthermore, in the growing period of the apples and the pears, an operation called "thinning out" is carried out. That is to say, a part of the fruits are thinned out and the other fruits are left as they are, when the fruits are still unripe, and therefore, the unripe fruits are easily available. The employment of the unripe fruits is also preferable from the viewpoint of the effective utilization of these useless unripe fruits.

The pressed juice or the extract of the fruits can be prepared as follows.

As a pressing method, for example, there can be employed a method which comprises washing a raw material, grinding and pressing the same while sulfurous acid is added thereto to obtain the pressed juice, preferably adding a pectolysis enzyme, and then using a means such as centrifugal separation or filtration to obtain a cleaned fruit juice.

As an extraction method, for example, there can be employed a method which comprises mixing a washed material with an alcohol (ethanol, methanol or the like), grinding the same, allowing the mixture to stand for impregnation, pressing or extracting it under heating and refluxing, concentrating it under reduced pressure to distill off the alcohol, and then carrying out centrifugal separation or filtration, or carrying out partition and filtration with an organic solvent (hexane, chloroform or the like) to obtain the cleaned fruit juice.

The purification of the polyphenol can be carried out by using an adsorbent capable of selectively adsorbing and eluting the polyphenol, for example, a styrene-divinylbenzene-based synthetic adsorption resin, an anion exchange resin or an octadecyl group chemical bonding type silica (ODS). That is to say, the cleaned fruit juice or the cleaned extract is passed through a column packed with such a resin, whereby the polyphenol is adsorbed by the resin. Next, distilled water is passed therethrough to wash the resin, and a 20–100% alcohol (e.g., ethanol) solution, preferably an about 50% alcohol solution is then passed through the column to elute and recover the polyphenol. The thus obtained polyphenol solution is concentrated under reduced pressure to distill off the alcohol, thereby obtaining the concentrated polyphenol solution. Furthermore, if necessary, a powder auxiliary such as a dextrin is added, and spray drying or freeze-drying is then carried out to obtain a polyphenol powder.

A typical example of the cosmetics of the present invention is a moisture cream comprising 100 wt % consisting of 2.0 wt % of monostearic acid polyethylene glycol, 5.0 wt % of monostearic acid glycerin, 5.0 wt % of stearic acid, 65.05 wt % of biphenyl alcohol, 15.0 wt % of squalane, 5.0 wt % of cetyl 2-ethylhexanoate, 0.1 wt % of butylparaben, 0.1 wt % of methylparaben, 5.0 wt % of 1,3-butylene glycol and purified water as well as suitable amounts of a perfume and the above-mentioned polyphenol.

Furthermore, examples of the quasi-drugs include medicinal cosmetics containing ascorbic acid phosphoric acid ester magnesium or dipotassium glycyrrhizate as an effective component, medicinal toothpastes containing acetylpyridium chloride and sodium chloride as the effective components, and bath agents containing sodium hdyrogencarbonate and dry sodium sulfate as the effective components, which contain the above-mentioned polyphenol. Here, ascorbic acid phosphoric acid ester magnesium has a beautiful whitening activity, and dipotassium glycyrrhizate is a component having an antiinflammatory activity. Furthermore, when acetylpyridium chloride, sodium chloride, sodium hydrogencarbonate and dry sodium sulfate are blended with the toothpastes or the medicinal toothpastes, the outbreak and the progress of gingivitis, pyorrhea and dental caries can be prevented, and halitosis can also be prevented. When they are blended with the skin cosmetic material, the hair cosmetic material or the like, they have a therapeutic effect for prickly heat, dry skin, bruise, stiff neck, sprain, neuralgia, eczema, frostbite, hemorrhoids, poor circulation, lumbago and the like.

If necessary, some additives which have been used in the usual cosmetics can suitably be added to the cosmetics of the present invention, and examples of the additives include an aqueous component, a powder, a surface active agent, an oil medicine, a humectant, an alcohol, a pH adjustor, an antiseptic substance, a dyestuff, an antioxidant, a thickener and a perfume. The cosmetics of the present invention can be prepared in the form of a milky lotion, a cream, a face toilet lotion, a facial pack, an ointment, a dispersant, a detergent or the like.

Next, the present invention will be described in more detail with reference to examples, but the scope of the present invention should not be limited to these examples.

EXAMPLE 1

(Preparation example of fruits polyphenol)

About 50 kg of unripe apples (5 to 10 g/apple) was ground by a grinder while a suitable amount of $SO_2$ was added thereto, and then pressed by an oil press. Afterward, about 50 ppm of a pectolysis enzyme was added to the resulting fruit juice, and it was subjected to centrifugal separation or diatomaceous earth filtration, followed by precision filtration, thereby obtaining 35 liter(l) of a cleaned fruit juice. Next, this cleaned fruit juice was further passed through a column packed with a styrene-divinylbenzene-based industrial synthetic adsorption resin (6 liter). Moreover, 6 liter of water containing 0.1% of HCl was passed through the column to eliminate saccharides, and elution was then carried out with 50% ethanol containing 0.1% of HCl to obtain 3 liter of a main polyphenol fraction.

The thus obtained fraction was concentrated under reduced pressure by an evaporator into 1.5 liter of the concentrated fraction. Next, this concentrated fraction was dried by a spray dryer to obtain 228.2 g of a polyphenol powder of the unripe apples.

The data regarding recovery are as follows.

Column recovery: 95.6%

Spray drying recovery: 93.0%

Recovery from fruit juice: 0.65%

Powder recovery from polyphenol in fruit juice: 88.9%

EXAMPLE 2

(Ultraviolet light absorbing activity of fruits polyphenol)

The ultraviolet light absorbing activity of the unripe apples polyphenol obtained in Example 1 was measured, and the measured activity of the polyphenol was compared with those of a tea extract and PABA which was a known ultraviolet light absorbing substance.

The ultraviolet light absorbing activity was measured by first dissolving each of the above-mentioned samples in 99.5% ethanol so that the concentration of the sample might be 10 $\mu$g/ml, and then measuring an absorption spectrum in an ultraviolet region (UV-B and UV-A) of 280 to 400 nm by a spectrophotometer (a Hitachi U-200 double beam type spectrophotometer).

The results are shown in FIG. 1. It is apparent that the unripe apples polyphenol had a wide ultraviolet absorption region and an absorbing power (0.178 at 320 nm and 0.070 at 350 nm) in a long wavelength region (UV-A) of 320 nm or more, where PABA which was the known ultraviolet light absorbing substance scarcely had the absorption.

EXAMPLE 3

(Free radical erasing activity of fruits polyphenol)

The free radical erasing activity of the polyphenol obtained in Example 1 was measured. The measurement was carried out in accordance with an ESR method as follows.

In the first place, 50 ml of a 0.1M phosphate buffer solution (pH=7.8) was added to 0.5 g of the polyphenol and then dissolved under ice cooling to prepare a test solution.

50 $\mu$l of a 2 mM hypoxanthine-phosphate buffer solution, 35 $\mu$l of a 5.5 mM DETAPAC (diethylenetriaminepentaacetic acid )-phosphate buffer solution, 50 $\mu$l of the test solution, 15 $\mu$l of a DMPO (5,5-dimethyl-1-pyrroline-1oxide) and 50 $\mu$l of a xanthine oxidase-phosphate buffer solution were mixed, and the mixture was then sucked by a specific flat cell (about 160 $\mu$l). Next, this cell was set to an ESR device, and after 40 seconds, sweep was begun. A ratio between the peak height of $Mn^{2+}$ (internal standard) and that of a measured signal was calculated.

On the basis of a calibration curve prepared by the use of an SOD standard solution (0 to 20 units/ml), the free radical erasing activity of the polyphenol was calculated.

In this case, as the ESR device, a JES-FR80 model made by JEOL, Ltd. was used. Furthermore, the ESR device was operated under the following conditions.

| | |
|---|---|
| Temperature | Room temperature |
| Microwave output | 8 mW |
| Magnetic field | 335.4 mT ± 5 mT |
| Modulation | 100 kHz, 0.79 × 0.1 mT |
| Amplification factor | 2 × 100 |
| Response time | 0.1 sec |
| Sweep time | 2 min |

As a result of the measurement, it is apparent that the unripe apples polyphenol showed the free radical erasing activity as high as $1.7 \times 10^5$ units/g.

The cosmetics of the present invention contain a polyphenol derived from the fruits of the Rosaceae and having many physiological activities such as an ultraviolet light absorbing activity, a free radical erasing activity, a deodorant activity and an antiallergic activity, and therefore the cosmetics are equipped with many functions such as the ultraviolet light absorbing function and the free radical erasing function.

What is claimed is:

1. A cosmetic composition comprising (1) a cosmetic base and (2) an effective amount of at least one polyphenol obtained from the unripe fruits of Rosaceae namely unripe apples, unripe pears or unripe peaches.

2. The cosmetic composition according to claim 1, wherein the polyphenol derived from the fruits of the Rosaceae is obtained by purifying a pressed juice or an extract of the unripe fruits of the Rosaceae.

3. The cosmetic composition according to claim 1, wherein the polyphenol derived from the fruits of the Rosaceae has a maximum ultraviolet light absorption wavelength in the range of 280 to 290 nm and in the range of 315 to 325 nm.

4. The cosmetic composition according to claim 1, wherein the polyphenol derived from the fruits of the Rosaceae has a free radical erasing activity of $1.0 \times 10^1$ to $1.0 \times 10^6$ units/g as measured by an electron spin resonance method.

5. The cosmetic composition according to claim 1, wherein the cosmetic base is a skin cosmetic material.

6. The cosmetic composition according to claim 5, wherein the cosmetic base comprises monostearic acid polyethylene glycol, monostearic acid glycerin, stearic acid, biphenyl alcohol, squalane, cetyl 2-ethylhexanoate, butylparaben, methylparaben, 1,3-butylene glycol and purified water and purfume.

7. The cosmetic composition according to claim 1, wherein the cosmetic base is a hair cosmetic material.

8. The cosmetic composition according to claim 1, wherein the cosmetic base is a toothpaste material.

9. A cosmetic composition according to claim 1 wherein the polyphenol derived from the fruits of Rosaceae contains simple polyphenol compounds including caffeic acid derivatives, p-coumaric acid derivatives, flavan-3-ols, flavonols, dihydrochalcones, and condensed tannins.

* * * * *